United States Patent [19]

Theeuwes

[11] 4,439,183
[45] Mar. 27, 1984

[54] PARENTERAL AGENT DISPENSING EQUIPMENT

[75] Inventor: Felix Theeuwes, Los Altos, Calif.

[73] Assignee: ALZA Corporation, Palo Alto, Calif.

[21] Appl. No.: 377,831

[22] Filed: May 13, 1982

Related U.S. Application Data

[63] Continuation-in-part of Ser. No. 310,047, Oct. 9, 1981.

[51] Int. Cl.³ ............................................. A61M 5/14
[52] U.S. Cl. ..................................... 604/85; 604/251
[58] Field of Search ............................ 604/56, 80–85, 604/251, 252, 890, 892

[56] References Cited

U.S. PATENT DOCUMENTS

| Re. 25,129 | 2/1962 | Walter | 604/252 X |
|---|---|---|---|
| 3,001,525 | 9/1961 | Hendricks | 604/251 X |
| 3,625,214 | 12/1971 | Higuchi | 604/892 |
| 3,847,150 | 12/1974 | Scheuerman | 604/84 |
| 3,941,126 | 3/1976 | Dietrich et al. | 604/83 X |
| 3,976,068 | 8/1976 | Lundquist | 604/56 X |
| 4,203,439 | 5/1980 | Theeuwes | 604/892 |
| 4,217,894 | 8/1980 | Franetzki | 604/84 X |
| 4,233,973 | 11/1980 | Shukla | 604/84 |
| 4,235,236 | 11/1980 | Theeuwes | 604/892 |
| 4,290,426 | 9/1981 | Luschen et al. | 604/892 |

*Primary Examiner*—Dalton L. Truluck
*Attorney, Agent, or Firm*—Paul L. Sabatine; Edward L. Mandell

[57] ABSTRACT

A parenteral delivery system and a formulation chamber are disclosed for administering a beneficial agent. The parenteral delivery system comprises a drip chamber and a formulation chamber. The formulation chamber comprises a wall surrounding an internal space and it has an inlet for admitting a liquid into the formulation chamber and an outlet for letting an agent formulation leave the formulation chamber. The chamber houses an agent delivery system for releasing a beneficial agent into a liquid that enters the chamber.

6 Claims, 9 Drawing Figures

FIG. 1
FIG. 2
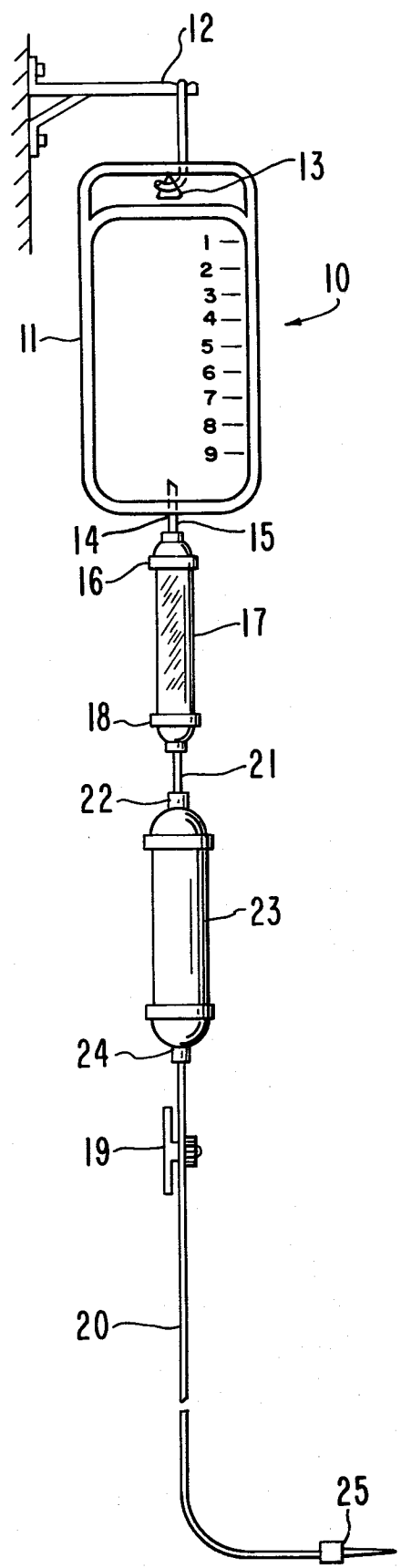
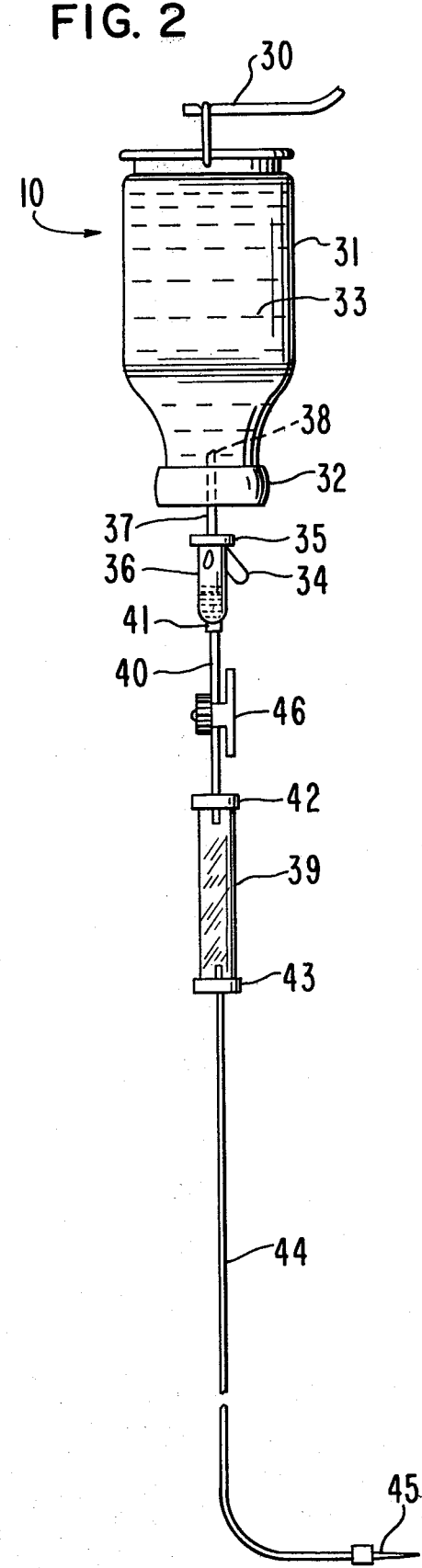

FIG. 3
FIG. 4
FIG. 5
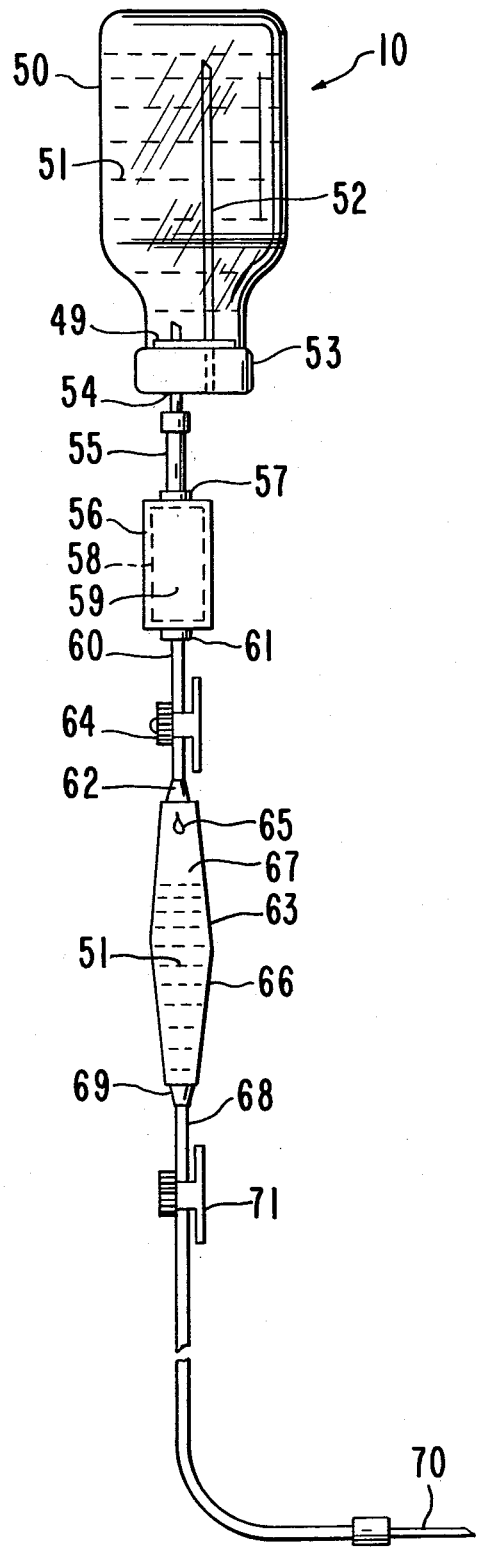
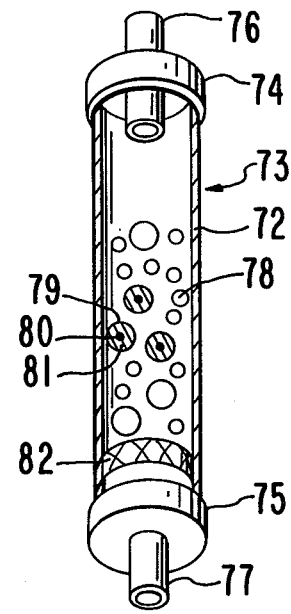
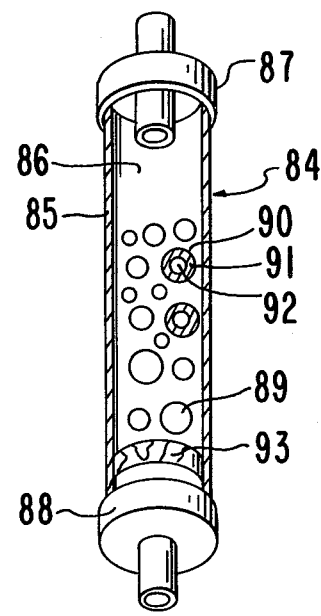

PARENTERAL AGENT DISPENSING EQUIPMENT

CROSS REFERENCE TO RELATED APPLICATION

This application is a continuation-in-part of patent application United States Ser. No. 310,047 filed on Oct. 9, 1981, which application is incorporated herein by reference. This application is copending with patent application United States Ser. No. 312,491 filed on Oct. 19, 1981. All of these applications are assigned to the ALZA Corporation of Palo Alto, Calif.

FIELD OF THE INVENTION

This invention pertains to parenteral dispensing equipment comprising a formulation chamber containing an agent delivery system. The invention also relates to a method of parenterally administering a beneficial agent using the parenteral equipment housing the delivery system.

BACKGROUND OF THE INVENTION

The parenteral administration of medical liquids is an established clinical practice. The liquids are administered usually intravenously, and the practice is used extensively as an integral part of the daily treatment of medical and surgical patients. The fluids administered parenterally, usually intravenously, include aqueous solutions of dextrose, sodium chloride and various other therapeutically acceptable electrolytes. The liquids or fluids commonly administered intravenously include blood, blood substitutes, and plasma substitutes. Generally, the fluids are administered from a container suspended above the patient, with the fluid flowing through a catheter hypodermic needle set to the patient. The needle is placed in a blood vessel, usually a vein of a patient for intravenous administration. For the intraperitoneal administration of fluids, the administration set is connected to a cannula transversing the abdominal wall of the patient.

The administration of fluids parenterally is a valuable and important component of patient care; moreover, the use of parenteral fluids has in recent years expanded beyond its original role of fluid and electrolyte replacement to include serving as the vehicle for the parenteral administration of beneficial agents, mainly those which are desirable to administer by infusion through intravenous, intra-arterial, intraperitoneal or subcutaneous routes. For example, presently a beneficial agent, such as a drug, is administered intravenously by one of the following procedures: temporarily halting the flow of medical fluid and intravenously administering the drug to the patient through an injection port in the administration set, followed by resumption of medical fluid into the patient; a drug is added to the fluid in the container, or into a volume control chamber in series with the administration set, and then carried by the flow of fluid to the patient; a drug is introduced into a so-called "piggyback" container which is subsequently connected by a connector, in tributary fashion, to the primary administration set through which the medical fluid is administered to the patient; or a drug is administered by a pump which, by one of various recognized mechanical pumping actions, establishes flow and this determines the flow of fluid containing the drug into a flow path entering the patient, for example, an indwelling venous catheter.

While these delivery techniques are being used, they inherently possess certain disadvantages. For example, the administration of a drug through repeated injections into the administration set is inconvenient and represents each time a potential break in sterility; the use of pumps is expensive and sometimes inconvenient because of their size and weight; the rate of drug delivery to the patient is directly dependent on the flow of fluid with all currently practiced means of drug infusion; because of the relative chemical instability of aqueous solutions of many commonly used parenteral drugs, these procedures often require solubilization of the drug medication by the hospital pharmacist or nurse at a time, proximate to its administration. While it is current practice to give some drugs by brief infusion, typically of 30 minutes to two hours duration repeated three or four times a day, they do not provide a means for careful coordination of the procedures for solubilization and administration, and for careful regulation of the flow of drug solution during each period of infusion to insure that infusion is completed within the recommended time.

In view of this presentation, it is immediately apparent a critical need exists for a dependable and practicable parenteral therapeutic delivery system that overcomes the disadvantages associated with the systems known to the prior art. It is also apparent that a pressing need exists for a parenteral delivery system that can be used clinically for administering parenterally a beneficial agent at a controlled rate and in a beneficially effective amount to a patient over a prolonged period of time.

DISCLOSURE OF THE INVENTION

Accordingly, a principal object of this invention is to provide a parenteral delivery system for administering a beneficial agent at a controlled rate and in an improved manner for optimizing the care of a host whose prognosis benefits from parenteral therapy.

Another object of the present invention is to provide a parenteral delivery system comprising a formulation chamber housing a delivery system containing a beneficial agent for delivering the agent into a parenteral fluid that enters the chamber for optimizing the care of a patient on parenteral therapy.

Another object of the invention is to provide a formulation chamber containing a drug delivery system, wherein the chamber is adapted, shaped and sized for use in a parenteral delivery system and wherein the device is designed for admitting a beneficial agent at a controlled rate into a parenteral fluid admitted into the formulation chamber.

Another object of the invention is to provide an agent formulation chamber adapted for use with an intravenous delivery system which chamber houses an agent delivery device for admitting an agent at a rate essentially controlled by the device into an intravenous fluid admitted into the formulation chamber.

Another object of the invention is to provide an intravenous therapeutic system comprising a container and a drug formulation chamber that house a delivery system for delivering a drug at a rate governed by the device into a medical fluid that flows from the container into the chamber and hence to a drug recipient.

Another object of the invention is to provide an intravenous delivery system comprising a formulation chamber housing an agent delivery system having a total surface area of a high magnitude for releasing a large amount of agent in a limited time into a limited volume to perform a preselected agent program.

Another object of the invention is to provide a formulation chamber housing an agent delivery system comprising a high membrane surface area for achieving high agent release rates over time.

The invention concerns both a parenteral delivery system and an agent formulation chamber. The parenteral delivery system comprises a container for storing a medical fluid which is also a pharmaceutically acceptable carrier for the agent, a drip chamber, a formulation chamber, and a conduit for conveying the medical fluid to a recipient. The formulation chamber comprises a wall surrounding a lumen and inlet that permits communication with the container and an outlet that permits communication with the parenteral system. The formulation chamber houses a delivery system containing a beneficial agent that is released at a rate controlled by the delivery system over time. The agent on its release is formulated in situ with a medical fluid that enters the chamber with the agent-fluid formulation then infused into a recipient. The agent delivery system, or dosage form, stores an amount of beneficial agent for executing a prescribed beneficial program, and it provides for the preprogrammed, unattended delivery of a beneficially or a therapeutically effective amount of the agent to produce a beneficial or a therapeutic result.

BRIEF DESCRIPTION OF THE DRAWINGS

In the drawings, which are not drawn to scale, but are set forth to illustrate various embodiments of the invention, the Figures are as follows:

FIG. 1 is a perspective view showing an embodiment of the invention comprising a parenteral delivery system comprising a formulation chamber;

FIG. 2 is a perspective view showing another embodiment of the invention comprising a parenteral delivery system comprising a formulation chamber;

FIG. 3 is a perspective view of still another embodiment of the invention comprising a parenteral delivery system for delivering a beneficial agent solution;

FIG. 4 is a view of a formulation chamber housing a delivery system comprising a multiplicity of tiny timed pills;

FIG. 5 is a view of a formulation chamber seen in opened section depicting the chamber housing a delivery system comprising a plurality of tiny capsules containing a beneficial agent;

In the specification and the drawings, like parts in related Figures are identified by like numbers. The terms appearing earlier in the specification and in the description of the drawings are described hereafter in the disclosure.

MODES FOR CARRYING OUT THE INVENTION

Figure 6:
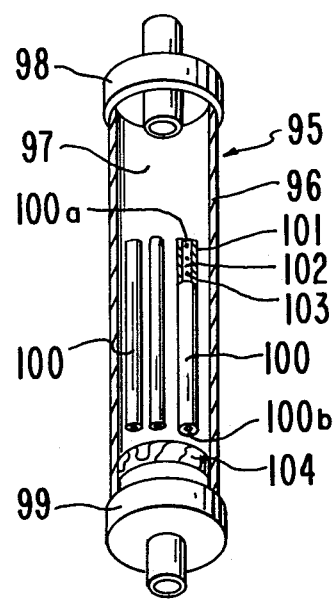
FIG. 6 is a view of a formulation chamber housing a delivery system comprising a multiplicity of hollow fibers filled with beneficial agent.

FIG. 1 illustrates an operative parenteral delivery system provided by the invention and it is generally designated by the numeral 10. Parenteral system 10 comprises a container 11 formed of a flexible, or a semi-rigid, preferably transparent plastic, such as a polyolefin, or polyvinylchloride, and it can contain a medical fluid adapted for parenteral including intravenous administration. The medical fluid will typically be a sterile solution, such as an aqueous solution of dextrose, a solution of dextrose in saline, saline, and an electrolyte solution. The medical fluid also is a pharmaceutical vehicle or carrier for a beneficial agent that is to be administered to a recipient, and as a pharmaceutical carrier it is acceptable for intravenous administration. Container 11, in the embodiment illustrated, is non-vented, a medical fluid in the container is at atmospheric pressure, and the container collapses as it empties of medical fluid. Container 11 usually is adapted to be hung neck-down from a hanger 12 by a bib or hole 13 that is connected, or it is integrally formed as part of container 11. Container 11, at its end distant from its hanging end, that is, at its neck end, has an administration port 14 adapted for receiving an administration set.

The administration set provided by this invention is used to deliver a fluid from container 11 and a beneficial agent admitted into parenteral delivery system 10 to a patient. The administration set is sterile, pyrogenfree, and preferably disposable. The administration set comprises the components described hereafter, and it connects with port 14 of container 11. Port 14 can be a diaphragm in container 11, not shown, or port 14 can be a hollow connector 15 that pierces the wall of container 11. Connector 15 is adapted to receive inlet end 16 of drip chamber 17, which end 16 snugly receives connector 15 and fits snugly over the main body forming drip chamber 17. Drip chamber 17 has another end 18 that fits snugly over the main body of drip chamber 17. End 18 is an outlet end that establishes fluid communication between dip chamber 17 and the rest of parenteral system 10. Drip chamber 17 is used to trap air and it permits adjustment of the rate of fluid flow from container 11 as the flow proceeds dropwise. Drip chamber 17 comprises a wall surrounding a lumen and the drip rate is governed by adjustable clamp 19 on second segment tubing 20. Clamp 19 pinches the internal diameter of tubing 20 to regulate flow in cooperation with drip sight chamber 17. An outlet 18 of drip chamber 17 is connected to a first segment tubing 21 that fits into outlet 18. Tubing 21 connects in fluid communication to inlet 22 of agent formulation chamber 23. Tubing 20 connects to outlet 24 of formulation chamber 23 and to an adapter-needle assembly 25 that is inserted into a vein and sometimes an artery of a warm-blooded animal.

Agent formulation chamber 23 is sized, shaped and adapted for use in a parenteral system, it is self-contained, self-powered, and amenable to low cost manufacturing. Formulation chamber 23 as seen in FIG. 1 comprises a wall-forming member that surrounds an internal lumen and it is capped at its ends by inlet 22 and outlet 24. Formulation chamber 23 houses an agent delivery system for introducing a beneficial agent into a medical fluid introduced in said chamber. The use of formulation chamber 23 with the delivery system housed therein does not require any reconstitution or admixture prior to use. Formulation chamber 23 is a light weight and disposable. Inlet 22 and outlet 24 are made for receiving tubes 21 and 20. Formulation chamber 23 is made of glass, plastic or the like, and as illustrated it is made of a transparent material for illustrating its structure and a delivery system housed therein. The agent delivery system present in formulation chamber 23 includes tiny timed pills, microcapsules, fibers, and erodible delivery systems, a presentation of said system appears later in the specification. Agent formulation chamber 23 generally will have a capacity of from about 10 milliliters to 250 milliliters of fluid or more, while simultaneously housing an agent delivery system. The term fluid or liquid as used herein denotes a fluid or a liquid that can be administered parenterally including intravenously, comprising pharmaceutically acceptable fluids that are also a pharmaceutically acceptable carrier for an agent, such as water, isotonic saline, Ringer's lacetate solution, and the like. The expression beneficial agent, as used herein, generically denotes any substance that on release by the delivery system produces a therapeutic or a beneficial result, such as a drug, a carbohydrate, an electrolyte, and/or the like. The term formulation, and agent formulation as presently used herein, generically indicates the beneficial agent on release by the delivery system is formulated, mixed, added, dissolved, suspended, carried, and/or the like in or by the fluid in a physical-chemical form acceptable for parenteral including intravenous administration. In addition, formulation chamber 23 can simultaneously serve as a drip chamber while housing the delivery system. In this embodiment, the formulation chamber-drip chamber is used to achieve a desired fluid drip rate. For example, the formulation chamber-drip chamber can have a fast drip rate for adults, or it can have a slower drip rate for pediatric use. The formulation chamber-drip chamber can be made with various sized inlets for controlling the rate of drip, or the drip can be controlled by regulating the clamp on the tubing. The formulation chamber-drip chamber can deliver, for example, from 2 to 75 drops per milliliter over from 1 minute to 1 hour. More preferably, the therapist can adjust the rate of flow to 1 to 20 drops per minute, or for the need of the patient. An additional disclosure pertaining to formulation chamber 23 is presented later in the specification.

FIG. 2 illustrates another operative parenteral therapeutic system generally designated 10 as provided by the invention. System 10 is supported in delivery position by support 30. System 10 is a vented-type system that requires air to operate. System 10 comprises a container 31 made of glass or rigid clear plastic suitably sealed with a rubber stopper, not shown, that is held in container 31 by annular closure rim 32. Container 31 contains a fluid 33 designated preferably for intravenous administration. Air enters system 10 through air inlet 34 formed as part of the inlet closure 35 of drip chamber 36. A spike 37 that is hollow pierces the rubber closure of container 31 and it serves as a conduit for letting air travel from air inlet 34 into container 31 and as a conduit for letting fluid 33 travel from container 31 into drip chamber 36. One point 38 of spike 37 is seen in container 31, the other point of spike 32, not seen, enters drip chamber 36 for conveying fluid 33 from container 31 to drip chamber 36. Drip chamber 36 is of conventional, hollow, tubular-like design consisting of a wall surrounding an internal fluid receiving lumen and it is connected to an agent formulation chamber 39 through a first section of tube 40 inserted into its outlet end 41 of drip chamber 36, and it also is inserted into formulation chamber end 42 adapted for receiving tube 40. The other end 43 of formulation chamber 39 is adapted for receiving a second section of tube 44. Formulation chamber 39 is made of glass or plastic, and it is preferably transparent. Formulation chamber 39 can have any shape adapted for use in a parenteral delivery system including intravenous delivery systems, and it is preferably round and its length exceeds its width. Ends 42 and 43 fit snugly over the wall of chamber 39 to form an air-tight, leak-proof closure for housing a delivery system that releases an agent for forming an agent solution in situ, in chamber 39 with fluid 33 entering chamber 39 from container 31 by mixing or dissolving therein. Tubing 44 conveys solution containing agent from chamber 39 to needle 45 for administration to a host. A regulating clamp 46 is provided on tube 40 for pinching the internal diameter of tube 40 for regulating the flow of fluid 33 through the system 10.

FIG. 3 illustrates another intravenous system 10 provided by this invention. System 10 comprises a container 50 that is a reservoir of a pharmaceutically acceptable fluid 51 that is also a pharmaceutically acceptable carrier for a useful agent, and it has a venting tube 52 which allows air to enter container 50 as medical fluid 51 is infused into a patient. Container 50 is closed with a stopper 49, and it has a hole for venting tube 52. Closure rim 53 around container 50 holds stopper 49 in container 50. Container 50 is connected through a hollow spike 54 adaptor to the intravenous system for sending medical fluid 51 from container 50 through system 10 to a patient. Spike 54 connects to a first section of tubing 55 that enters formulation chamber 56 at its inlet 57. Formulation chamber 56 comprises a wall 58 that surround an internal space 59. Formulation chamber 56 houses in space 59 a drug delivery system, seen in later figures, for performing a beneficial program. An agent on release from the delivery system is present in a pharmaceutically acceptable form that can undergo dissolution, or it can disintegrate into smaller parts and dissolve in the presence of liquid that enters opened-view formulation chamber 56 to form in chamber 56 an agent solution. A second section of tubing 60 connects outlet end 61 of chamber 56 with inlet 62 of opened-view drip chamber 63. Tubing 60 passes through a first clamp 64 used for regulating flow from container 50 through formulation chamber 56 and into drip chamber 63. Drip chamber 63 is as previously described, made preferably of a see through material such as glass or plastic for visibly counting a measurable number of drops 65 that pass through said drip chamber 63 in unit time. Drip chamber 63 is seen in opened view and it comprises a wall 66 that surrounds an internal space 67 containing fluid 51 that enters as drops 65. A second section of tubing 68 connects outlet 69 of drip chamber 63 with administration needle 70. Tubing 68 passes through a regulating clamp 71 used for regulating flow through system 10 to a patient. Regulating clamp 64 and regulating clamp 71 can be adjusted independently or they can be adjusted together to act as a unit regulator.

FIGS. 4 through 8 depict structural embodiments of formulation chambers housing delivery systems that can be used in the parenteral delivery systems of FIGS. 1 to 3. In FIG. 4 a formulation chamber 73 is illustrated with a section removed for depicting the inside of the chamber. The chamber is light weight, disposable, and indicated for use in patients requiring intravenous administration of a fluid containing a beneficial agent, such as an intravenously administrable drug. In FIG. 4, formulation chamber 73 comprises a walled body 72 of tube shape and it has a pair of caps 74 and 75 for forming a closed chamber containing fluid and a delivery system. Caps 74 and 75 fit chamber 73 and they are preferably made of self-sealing rubber through which a needle or a hollow spike can be inserted, or they can have an integrally formed tubular extension 76 and 77 for receiving an incoming tube. Hollow tubular member 76 and 77 are preferably round for receiving a tube that slides into, or slides over the member. Formulation chamber 73 is made of a material that is moisture proof, impermeable to microorganisms, ionizing ray permeable and adapted to house a delivery system and any incoming fluids, including aqueous and non-aqueous fluids.

The delivery system depicted in formulation chamber 73 comprises a multiplicity of tiny timed pills 78 for the controlled delivery of an agent, including drug, into a fluid entering chamber 73. The tiny pills are seen in detail, in opened section pills 79, and they comprise a core of drug 80 surrounded by a wall 81 formed of a release rate controlling material. The tiny timed pills 78 provide a high membrane surface area for achieving high release rates of agent for forming an agent solution. The total number of tiny pills 78 in formulation chamber 73 can be varied as an added means for regulating the amount of agent made available for forming an agent solution. The materials forming wall 81 can be selected from materials that release drug 80 by different physical-chemical mechanisms. These mechanisms include erosion, diffusion and osmosis mechanisms. Wall 81, when releasing drug by osmosis, released drug by bursting. Drug 80 in this embodiment is present in the form of an osmotic solute, such as a therapeutically acceptable salt, and it exhibits an osmotic pressure gradient across wall 81 against an external fluid. The membrane materials used to form wall 81 are those permeable to the passage of an external fluid and substantially impermeable to the passage of drug. Typical materials include a member selected from the group consisting of cellulose acylate, cellulose diacylate, cellulose triacylate, cellulose acetate, cellulose triacetate, and and like. The osmotic wall can be coated around the drug in varying thickness by pan coating, spray-pan coating, Wurster fluid air-suspension coating and the like. The wall is formed using organic solvents, including methylene chloride-methanol, methylene chloride-acetone, methanol-acetone, ethylene dichloride-acetone, and the like. Osmotic wall forming materials, procedures for forming the wall, and osmotic bursting procedures are disclosed in U.S. Pat. Nos. 2,799,241; 3,952,741; 4,014,334; and 4,016,880.

Wall 81 of tiny pills 78 in another embodiment can be made of a drug release rate controlling material. That is, drug 80 dissolves in the wall or through pores within the wall and passes through the wall or through said pores at a controlled rate by diffusion over time. Exemplary materials useful for forming a diffusional wall or a wall with pores include ethylene-vinyl acetate copolymer, ethyl cellulose, polyethylene, cross-linked polyvinyl pyrrolidone, vinylidene chloride-acrylonitrile copolymer, polypropylene, silicone, and the like. The wall can be applied by techniques described above, and materials suitable for forming wall 81 are described in U.S. Pat. Nos. 3,938,515; e,948,262; and 4,014,335.

Wall 81 of tiny pills 78 can be made of bioerodible material that bioerodes at a controlled rate and releases drug 80 to the fluid in chamber 73. Bioerodible materials useful for forming wall 81 include polycarboxylic acid, polyesters, polyamides, polyimides, polylactic acid, polyglycolic acid, polyorthoesters, and polycarbonates. These polymers and procedures for forming wall 81 are disclosed in U.S. Pat. Nos. 3,811,444; 3,867,519; 3,888,975; 3,971,367; 3,993,057; and 4,138,344. The amount of drug present in a tiny timed pill generally is about 10 ng. to 20 mg, and the number of tiny pills in a chamber is about 10 to 1000, preferably 50 to 150. The tiny pills comprising the wall and the inner core of drug have a diameter of at least 100 microns, and in a presently preferred embodiment a diameter of at least 2000 microns. The tiny pills can have one or more coatings of wall-forming materials thereon. Chamber 73 optionally is equipped with a support 82 for the tiny pills. Support 82 can be a film having a release rate controlling properties and made of a polymer that releases drug from chamber 73, support 82 can be a microporous polymeric membrane, a sintered glass support, a perforated grid, and/or the like.

FIG. 5 illustrates a formulation chamber 84 comprising a wall 85 surrounding a lumen 86 having an inlet 87 and an outlet 88. Chamber 84 houses a plurality of tiny capsules 89 further seen in opened section capsule 90. Capsules 90 comprise a wall 91 surrounding a mass of liquid drug 92. The tiny capsules can be made by coacervation technique consisting essentially of forming three immiscible phases, a liquid manufacturing phase, a core material phase and a coating phase. The coating phase is deposited as a liquid on the core material and rigidized usually by thermal, cross-linking or desolvation techniques, to form tiny microcapsules. The capsules made by this technique have an average particle size of from several tenths of a micron to 5,000 microns, and in some embodiments a larger tiny capsule can be used herein. Particle size however, is not critical in the practice of this invention. Suitable techniques for preparing tiny microcapsules are reported by Bungenberg de Jong and Kass, Biochem.Z., Vol. 232, pages 338 to 345, 1931; *Colloid Sience*, Vol. 11, "Reversible System," edited by H. R. Kruyt, 1949, Elsevier Publishing Co., Inc., New York; J. Pharm. Sci., Vol 59, No. 10, pages 1,367 to 1,376, 1970; and Pharmaceutical Science, Remington, Vol. XIV, pages 1,676 to 1,677, 1970, Mack Publishing Co., Easton, PA. Formulation chamber 84 also contains a film 93 that supports the tiny capsules and which film can also serve as a means for regulating the release of drug solution from formulation chamber 84.

FIG. 6 illustrates a formulation chamber 95 comprising a wall 96 that surrounds an internal lumen 97 with an inlet end 98 and an outlet end 99. Chamber 95 houses a multiplicity of hollow fibers 100, with one fiber seen in opened section comprising a wall 101, that can be formed of a semipermeable polymer, a diffusional polymer, a microporous polymer, a lamina, or a laminate of two or more lamina, surrounding a lumen 102 containing drug 103. The hollow fibers provide a large exposed surface area for concomitantly releasing a large amount of agent into the formulation chamber. The hollow fibers can have a length of a few millimeters to many centimeters or longer, a diameter of a millimeter or larger, and the chamber houses at least one hollow fiber to several hundred or more. The hollow fibers have openings at each end, 100a and 100b, can be produced from non-cellulosic polymers using melt spinning techniques using shaped spinnerettes. Hollow fibers can also be produced by spinning an organic solvent cellulosic solution into certain regenerants, n-octanol where the solvent is dialkylacylamide, and n-hexanol where the solvent is dimethylsulfoxide. The hollow fibers can be filled with drug by using a solution of drug injected into one opened end of the fiber, by soaking in a drug solution, and the like. The hollow fibers can release an agent by diffusion, dialysis, osmotic, leaching and like techniques. The amount of agent released from the fibers further can be regulated by selecting the dimensions and number of hollow fibers housed in the formulation chamber. A procedure for manufacturing hollow fibers is disclosed in U.S. Pat. No. 4,086,418. Formulation chamber 95 optionally contains a support 104 for holding the fiber which support permits the passage of drug formulation from chamber 95.

Figure 7:
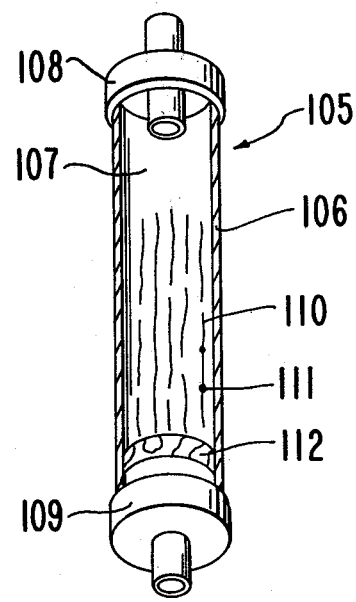
FIG. 7 is a view of a formulation chamber housing a delivery system comprising a plurality of solid fiber filled with beneficial agent.

FIG. 7 illustrates a formulation chamber 105, seen in opened section, and it comprises a wall 106 that surrounds a lumen 107 with an inlet 108 and an outlet 109 for admitting and exiting fluid from chamber 105. Chamber 105 houses a multiplicity of fibers 110 containing drug 111, represented by dots. The fibers 110 forming the drug delivery system can be of natural or synthetic origin, and they can have a wide variety of structures, such as solid, semi-solid, porous, and the like, a variety of geometric shapes such as round, oval, square, trilobal, various lengths and cross-sections, and the like. The fibers can function effectively as a reservoir by having drug dispersed therethrough. Suitable fibers can be made by conventional fabrication techniques. For example, fiber material and drug may be dissolved in a solvent, extruded through small holes of a die and then solidified by standard melt spinning, wet spinning, or dry spinning techniques. In another embodiment, the fibers can be produced by pumping a melt of fiber and drug through a spinneret. With such a method, fiber diameter may be varied from a few tenths to a micron to a millimeter or so by down-drawing, or by up-drawing techniques. The lumen of the chamber can house fibers of mixed denier. The fibers forming the reservoir can be filled, saturated, or semi-filled with drug by immersing, soaking or the like and permitting the desired amount of drug to transfer into the fibers. Other techniques and drugs for forming fibers are disclosed in U.S. Pat. Nos. 3,228,887 and 3,921,636. The materials forming the fibers can be polyolefins, polyamides, polyurethanes, cellulosic materials and the like. Fiber procedures are set forth in Encyclopedia of Science and Technology, Vol. 5, pages 263 to 276, 1971, published by McGraw Hill Co., New York. Chamber 105 also contains a membrane 112 for supporting the fibers and it can be formed of a diffusional or porous polymer for cooperating with the fibers for regulating the amount of drug solution infused into a patient.

Figure 8:
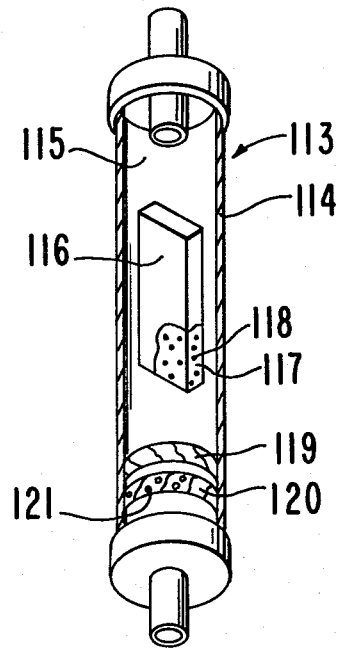
FIG. 8 is a view of a formulation chamber housing a delivery system comprising a drug delivery system consisting of a bioerodible polymer housing beneficial agent.

FIG. 8 illustrates a formulation chamber 113 having a section of its wall 114 removed for depicting the internal space 115 as a means for housing for a beneficial agent delivery system 116. System 116 comprises a reservoir formed of an erodible polymer, and a section is removed 117 for illustrating agent 118 dispersed therein. The erodible polymer can be a member selected from the group including polyorthoesters, polyorthocarbonates, polyglycolic acid, polylactic acid, polyacetals, polyketals, polyamino acids, and the like. Procedures and erodible polymers are disclosed in U.S. Pat. No. 4,180,646; in Int. J. of Pharmaceutics, Vol. 7, pages 1 to 18, 1980; in Biodegradables and Delivery Systems for Contraception, Chapter 2, edited by E. S. E. Hafex and W. A. A. Van Os, published by G. K. Hall, Boston, 1980. Chamber 113 can also have a release rate controlling polymeric film 119 such as cellulose acetate or the like, and a filter 120. Filter 120 is a conventional filter with a pore 121 having pore size of 0.1 micron to 5 micron, and more preferably 0.22 micron or 0.45 micron, for removing bacterial and unwanted matter from flowing solution, thereby aiding in maintaining a sterile solution.

Figure 9:
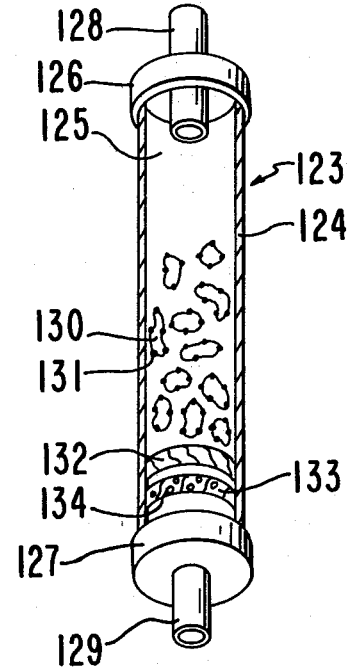
FIG. 9 is an opened view of a formulation chamber housing a plurality of ion-exchange members with active agent ionically bonded thereto.

FIG. 9 illustrates a formulation chamber 123 in opened-view comprising a wall 124 surrounding an internal space closed at its inlet end with cap 126 and at its outlet end with cap 127. Cap 126 has a tube receiving member 128 and can 127 has a tube receiving member 129 for letting a fluid into and out of formulation chamber 123. Formulation chamber 123 houses an agent delivery system comprising a plurality of ion-exchange resin particles 130 having an agent 131 ionically attracted thereto. The resins can be particles, bead, and droplet shaped. The particles and the like can vary in size, usually from 10 to 350 mesh. The resins can be homopolymers, copolymers, derivatives thereof, or cross-linked resins. Typical resins include ion-exchange resins such as cross-linked styrene-divinyl benzene and the like, having agent 131 ionically bonded thereto. Active agent 131 is released from resin 130 into fluid that enters the formulation chamber to form in the chamber an agent solution for administering to a patient. Chamber 123 also can house a release rate controlling film 132 and a filter 133 having pores 134 for preventing bacteria and unwanted matter from leaving the formulation chamber. The ion-exchange resins are disclosed in U.S. Pat. No. 4,203,440.

The parenteral systems comprising the formulation chamber can be used, in one embodiment in fluid replacement, such as administering plasma, saline or the like, and simultaneously administering a therapeutically effective amount of agent, drug or prodrug therewith; in another embodiment as in a method of electrolyte balance replacement, such as supplying sodium, potassium, chloride ions, or the like with a drug in an active form, in an inactive form that is converted in the animal to an active form, or in a form that is made active in the drug formulation chamber and administered therewith to an animal, such as a human patient in need of electrolyte restoration and an intravenous drug; and in a method of intravenous nutrition, such as supplying dextrose and concomitantly administering a drug to a warm-blooded animal such as a patient in need of such therapies. The intravenous therapy system also can be used in the practice of verterinary medicine.

The novel and useful invention provides an apparatus and a method for the obtainment of precise control of agent release with a parenteral delivery system for administration to a warm-blooded animal. While there has been described and pointed out features of the invention as applied to presently preferred embodiments, those skilled in the art will appreciate that various modifications, changes, additions, and omissions in the invention illustrated and described can be made without departing from the spirit of the invention.

I claim:

1. A formulation chamber for use in a parenteral delivery system, comprising:
   (a) a wall surrounding an internal lumen;
   (b) an inlet for admitting a fluid into the chamber;
   (c) an outlet for letting a fluid leave the chamber; and,
   (d) an erodible delivery system in the chamber, comprising:

(1) a matrix formed of a parenterally-acceptable material that erodes in the presence of a parenteral fluid over time, and;
(2) a beneficial agent dispersed in the matrix that is delivered by the erodible delivery system into parenteral fluid that enters the formulation chamber.

2. The formulation chamber for use in a parenteral delivery system according to claim 1, wherein the chamber contains a separate film that aids in controlling the rate of release of agent formulation from the chamber.

3. The formulation chamber for use in a parenteral delivery system according to claim 1, wherein the chamber contains a separate porous film that aids in controlling the rate of release of agent formulation from the chamber.

4. The formulation chamber for use in a parenteral delivery system according to claim 1, wherein the chamber contains a perforated grid that supports erodible delivery system in the chamber.

5. The formulation chamber for use in a parenteral delivery system according to claim 1, wherein the parenteral delivery system comprises a drip chamber in fluid communication with the formulation chamber.

6. An intravenous delivery system for administering a beneficial agent intravenously to a human, comprising:
(a) a container of a pharmaceutically acceptable liquid;
(b) a drip chamber in fluid communication with the container for determining the rate of fluid flow through the intravenous system for the continuous drip administration of liquid; and,
(c) a formulation comprising:
(1) a wall surrounding a lumen;
(2) an erodible agent delivery system in the chamber comprising a matrix formed of a polymer containing agent dispersed therein, which matrix erodes in the presence of a pharmaceutically acceptable liquid that enters the formulation chamber; and,
(3) wherein the formulation chamber is in fluid communication with the drip chamber such that liquid flows into the formulation chamber and forms with agent released from the matrix an agent formulation over time.

* * * * *